(12) United States Patent
Kwon et al.

(10) Patent No.: US 11,830,627 B2
(45) Date of Patent: Nov. 28, 2023

(54) SYSTEM AND METHOD FOR PREDICTING DISEASE BASED ON BIOSIGNAL DATA AND MEDICAL KNOWLEDGE BASE CONVERGENCE

(71) Applicant: Electronics and Telecommunications Research Institute, Daejeon (KR)

(72) Inventors: Soon Hyun Kwon, Incheon (KR); Se Jin Park, Gyeonggi-do (KR); Jae Hak Yoo, Daejeon (KR); Jong Arm Jun, Daejeon (KR); Cheol Sig Pyo, Sejong-si (KR)

(73) Assignee: Electronics and Telecommunications Research Institute, Daejeon (KR)

(*) Notice: Subject to any disclaimer, the term of this patent is extended or adjusted under 35 U.S.C. 154(b) by 0 days.

(21) Appl. No.: 17/719,600

(22) Filed: Apr. 13, 2022

(65) Prior Publication Data

US 2022/0328199 A1    Oct. 13, 2022

(30) Foreign Application Priority Data

Apr. 13, 2021    (KR) .................. 10-2021-0048012
Oct. 27, 2021    (KR) .................. 10-2021-0144783

(51) Int. Cl.
*G06F 17/00*      (2019.01)
*G16H 50/70*      (2018.01)
(Continued)

(52) U.S. Cl.
CPC ....... *G16H 50/70* (2018.01); *G06F 16/24573* (2019.01); *G06F 16/254* (2019.01); *G06F 16/285* (2019.01); *G16H 50/30* (2018.01)

(58) Field of Classification Search
CPC ........ G16H 50/70; G16H 50/30; G16H 50/20; G16H 40/63; G06F 16/24573;
(Continued)

(56) References Cited

U.S. PATENT DOCUMENTS

2009/0156906 A1*   6/2009   Liebman ................ G16H 50/50
                                                                         600/300
2013/0085773 A1*   4/2013   Yao ........................ G16H 50/70
                                                                           705/2
(Continued)

FOREIGN PATENT DOCUMENTS

KR         10-2108829 B      5/2020

OTHER PUBLICATIONS

Sebastian Böttcher et al., Using multimodal biosignal data from wearables to detect focal motor seizures in individual epilepsy patients. In Proceedings of the 6th International Workshop on Sensor-based Activity Recognition and Interaction. Association for Computing Machinery, Article 3, 1-6. (Year: 2019).*

(Continued)

*Primary Examiner* — Greta L Robinson
(74) *Attorney, Agent, or Firm* — NSIP Law

(57) ABSTRACT

Provided is a system for predicting disease based on biosignal data and medical knowledge base convergence. The system includes a first system unit configured to receive, from a user terminal, biosignal data collected from at least one sensor for sensing a biosignal, and calculate a disease score from the biosignal data based on a pre-trained prediction model, a second system unit configured to provide medical knowledge data for the first system unit, analyze a query input from the user terminal to provide a corresponding response, and augment the medical knowledge data based on the query and response; and a unified distributed repository that includes a database for enqueuing the biosignal data, a manager database for storing additional information of a user, and a medical knowledge base for storing predetermined medical knowledge data.

14 Claims, 10 Drawing Sheets

(51) Int. Cl.
*G16H 50/30* (2018.01)
*G06F 16/28* (2019.01)
*G06F 16/25* (2019.01)
*G06F 16/2457* (2019.01)

(58) Field of Classification Search
CPC ...... G06F 16/254; G06F 16/285; G06F 16/25; G06F 16/28; G06F 16/2457
See application file for complete search history.

(56) References Cited

U.S. PATENT DOCUMENTS

| | | | |
|---|---|---|---|
| 2014/0343955 A1* | 11/2014 | Raman | G16H 50/20 |
| | | | 705/2 |
| 2017/0357760 A1 | 12/2017 | Han et al. | |
| 2018/0150608 A1 | 5/2018 | Kim et al. | |
| 2021/0142913 A1* | 5/2021 | Terao | G16H 50/30 |
| 2021/0196196 A1* | 7/2021 | Poon | G16H 20/60 |

OTHER PUBLICATIONS

Nickel, Maximilian, et al. "A Review of Relational Machine Learning for Knowledge Graphs." *Proceedings of the IEEE 104.1, arXiv:1503.00759v3 [stat.ML]* Sep. 28, 2015. pp. 1-23 (23 pages in English).

* cited by examiner

SYSTEM AND METHOD FOR PREDICTING DISEASE BASED ON BIOSIGNAL DATA AND MEDICAL KNOWLEDGE BASE CONVERGENCE

CROSS-REFERENCE TO RELATED APPLICATION

This application claims priority to and the benefit of Korean Patent Application No. 10-2021-0048012, filed on Apr. 13, 2021 and Korean Patent Application No. 10-2021-0144783, filed on Oct. 27, 2021, the disclosure of which is incorporated herein by reference in its entirety.

BACKGROUND

1. Field of the Invention

The present invention relates to a system and method for predicting disease based on biosignal data and medical knowledge base convergence.

2. Discussion of Related Art

In order to predict diseases in the Internet of Everything (IoE) environment, it is essential to incorporate a medical knowledge base such as personal information of disease prediction subjects, symptoms and characteristics of diseases, and know-how of medical staff, and biosignal data detected in real time.

Accordingly, it is necessary to develop a technology that converges limitations of a data-based machine learning analysis method, such as a lack of explanation of analysis results and a lack of multi-angle analysis information setting, with knowledge information of medical domains built in a medical knowledge base.

SUMMARY OF THE INVENTION

The present invention is directed to providing a system and method capable of predicting disease by converging biosignal data collected from an existing wearable biosignal sensor and a medical knowledge base.

However, the problems to be solved by the present invention are not limited to the problems described above, and other problems may be present.

According to a first aspect of the present invention, a system for predicting disease based on biosignal data and medical knowledge base convergence includes a first system unit configured to receive, from a user terminal, biosignal data collected from at least one sensor for sensing a biosignal, and calculate a disease score from the biosignal data based on a pre-trained prediction model, a second system unit configured to provide medical knowledge data for the first system unit, analyze a query input from the user terminal to provide a corresponding response, and augment the medical knowledge data based on the query and response, and a unified distributed repository that includes a database for enqueuing the biosignal data, a manager database for storing additional information of a user, and a medical knowledge base for storing predetermined medical knowledge data.

According to a second aspect of the present invention, a method of predicting disease based on biosignal data and medical knowledge base convergence includes receiving biosignal data collected from at least one sensor sensing biosignal through a user terminal, calculating a disease score from the biosignal data based on a pre-trained prediction model, generating medical knowledge data having a predetermined type based on the biosignal data and a user query, and providing a response corresponding to the user query based on the medical knowledge data stored in the medical knowledge base.

According to another aspect of the present invention for solving the above-described problems, a computer program is combined with a computer that is hardware to execute a method of predicting disease based on biosignal data and medical knowledge base convergence and stored in a computer-readable recording medium.

Other specific details of the invention are contained in the detailed description and the accompanying drawings.

According to the embodiment of the present invention described above, it is possible to solve the problem of predicting diseases using only the existing biosignal sensor data in the information and communications technology (ICT) environment and improve the accuracy of the prediction process through organic linkage with a medical knowledge base for each detailed procedure of a prediction process.

In addition, it is possible to increase validity of the overall prediction by reinterpreting the existing unexplainable data-based prediction results as domain-specific information through linkage with the medical knowledge base.

In addition, it is possible to use the embodiment of the present invention as a common system for providing a domain-specific analysis method by linking a sensing data-based analysis method and a knowledge base-based analysis method in a detailed procedure.

Effects of the present invention are not limited to the above-described effects, and other effects that are not described will be clearly understood by those skilled in the art from the following descriptions.

BRIEF DESCRIPTION OF THE DRAWINGS

The above and other objects, features and advantages of the present invention will become more apparent to those of ordinary skill in the art by describing exemplary embodiments thereof in detail with reference to the accompanying drawings, in which.

DETAILED DESCRIPTION OF EXEMPLARY EMBODIMENTS

Figure 1:
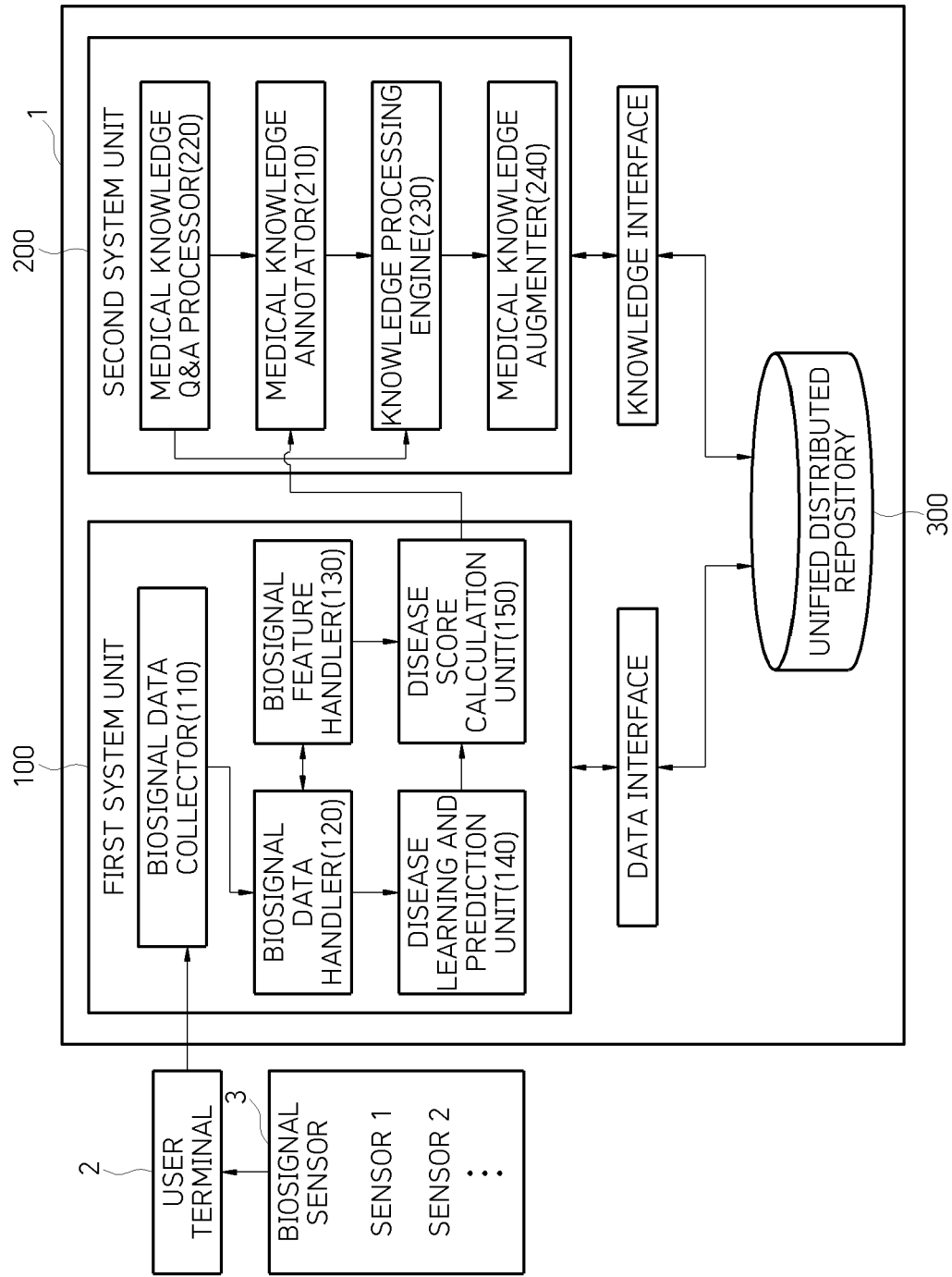
FIG. 1 is a block diagram of a disease prediction system according to an embodiment of the present invention.

Various advantages and features of the present invention and methods accomplishing them will become apparent from the following description of embodiments with reference to the accompanying drawings. However, the present invention is not limited to the embodiments disclosed herein but will be implemented in various forms. The embodiments serve to make the present invention thorough and are provided so that those skilled in the art can easily understand the scope of the present invention. Therefore, the present invention will be defined by the scope of the appended claims.

Terms used in the present specification are for explaining the embodiments rather than limiting the present invention. In the present invention, a singular form includes a plural form unless explicitly described to the contrary. Throughout this specification, the terms "comprise" and/or "comprising" will be understood to imply the inclusion of stated components but not the exclusion of any other constituents. Like reference numerals refer to like elements throughout the specification and "and/or" includes each of the stated components and includes all combinations thereof. Although "first," "second," and the like are used to describe various components, it goes without saying that these components are not limited by these terms. These terms are used only to distinguish one component from other components. Therefore, it goes without saying that the first component described below may be the second component within the technical scope of the present invention.

Unless otherwise defined, all terms (including technical and scientific terms) used in the present specification have the same meaning as meanings commonly understood by those skilled in the art to which the present invention pertains. In addition, terms as defined in a commonly used dictionary are not to be ideally or excessively interpreted unless explicitly defined otherwise.

The present invention relates to a system 1 and method for predicting disease based on biosignal data and medical knowledge base convergence.

Recently, after the fourth industrial revolution, as a paradigm of the health and medical field has changed from treatment after onset to prevention through early detection or detection of disease before onset, the concept and service of global health care are rapidly emerging. In particular, the digital healthcare and medical field in the global environment means a new healthcare solution that combines the latest information and communications technology (ICT) technologies such as big data, cloud computing, artificial intelligence, the Internet of Things, and medical technology. In the conventional medical services, patients may directly visit a hospital, etc. and receive medical services on the basis of specific symptoms and diagnosis of their health.

However, with the recent development of two-way communication technology transferred from ICT technologies including the Internet, patients may receive medical treatment and diagnosis remotely from medical staff in real time regardless of time and space. Recently, research on a monitoring service model capable of managing one's health condition by providing various types of biometric information such as blood pressure, electromyography, electrocardiography, and glucose sugar in real time in daily life is being actively conducted.

In particular, attempts to define and commercialize a service model that may be used for continuous monitoring of mental diseases such as chronic diseases, dementia, and depression based on the biometric information collected in real time are actively being conducted.

However, it is difficult for the ICT technology-based healthcare and medical diagnosis services to collect and analyze personal biometric information or signals in real time and perform real-time monitoring and disease prediction while having knowledge and diagnostic know-how of medical staff. Therefore, there is an urgent need for a system capable of providing medical services by predicting diseases and detecting symptoms early using medical knowledge and medical experience and know-how of medical staff about diseases, diseases, and symptoms.

In particular, in the field of disease prediction in the medical field, as a method of prediction and analysis through machine learning using data collected from the existing biosignal sensor does not take into account personal information of a subject of disease prediction, that is, age, gender, afflicted disease, smoking, drinking, or the like, and does not reflect characteristics of disease to be predicted, the method has limitations in analyzing accurate predicted values.

In addition, the method of predicting disease with only a medical knowledge base can derive general medical findings but has limitations in deriving personalized analysis results because real-time biometric information of a subject of disease prediction is not considered.

Therefore, for disease prediction, convergence of an analysis method through machine learning based on biosignal data and an analysis method based on a medical knowledge base is urgently needed, and methods to overcome and supplement the limitations of both the analysis methods are urgently needed.

In order to solve this problem, an embodiment of the present invention provides a method for predicting disease by building a prediction model based on machine learning using data collected from a wearable biosignal sensor in the existing Internet of Everything (IoE) environment, in the field of predicting disease in the ICT environment and builds a knowledge base of a medical knowledge domain, and links and maps individually collected biosignal data to the knowledge base to process the biosignal data, thereby increasing the prediction accuracy and providing a medical opinion on the prediction information together.

In this way, it is possible to overcome limitations of the prediction method through machine learning based on biosignal data without considering various medical findings and disease types and limitations of the analysis method through a knowledge base using only general medical opinion without considering real-time bio data for individual patients.

Hereinafter, a system 1 for predicting disease based on biosignal data and medical knowledge base convergence (hereinafter, disease prediction system) according to an embodiment of the present invention will be described with reference to FIGS. 1 to 8.

FIG. 1 is a block diagram of a disease prediction system 1 according to an embodiment of the present invention.

The disease prediction system 1 according to the embodiment of the present invention includes a first system unit 100, a second system unit 200, and a unified distributed repository 300.

Meanwhile, in the description of the present invention, it is suggested that a disease is a stroke for convenience, but it is not necessarily limited thereto. Accordingly, it goes without saying that various types of diseases that can be analyzed based on biosignal data may be a target.

The first system unit 100 receives, from the user terminal 2, biosignal data collected from at least one sensor 3 that detects a biosignal in real time. A disease score is calculated from the biosignal data based on a pre-trained prediction model. That is, the first system unit 100 predicts a stroke score which is a probabilistic value of a stroke.

The second system unit 200 provides medical knowledge data for the first system unit 100, analyzes a query input from the user terminal 2 to provide a corresponding response to a user, and augments medical knowledge data based on the query and response. That is, the second system unit 200 serves to easily perform a learning process of predicting a stroke with medical findings of a stroke stored in the medical knowledge base and a process of extending medical feature information and to present medical opinions on a result of a stroke score.

The unified distributed repository 300 includes a plurality of sensor data databases that enqueue biosignal data, a manager database that stores additional information of a user, and a medical knowledge base that stores predetermined medical knowledge data.

Specifically, the first system unit 100 includes a biosignal data collector 110, a biosignal data handler 120, a biosignal feature handler 130, a disease learning and prediction unit 140, and a disease score calculation unit 150.

Figure 2A:
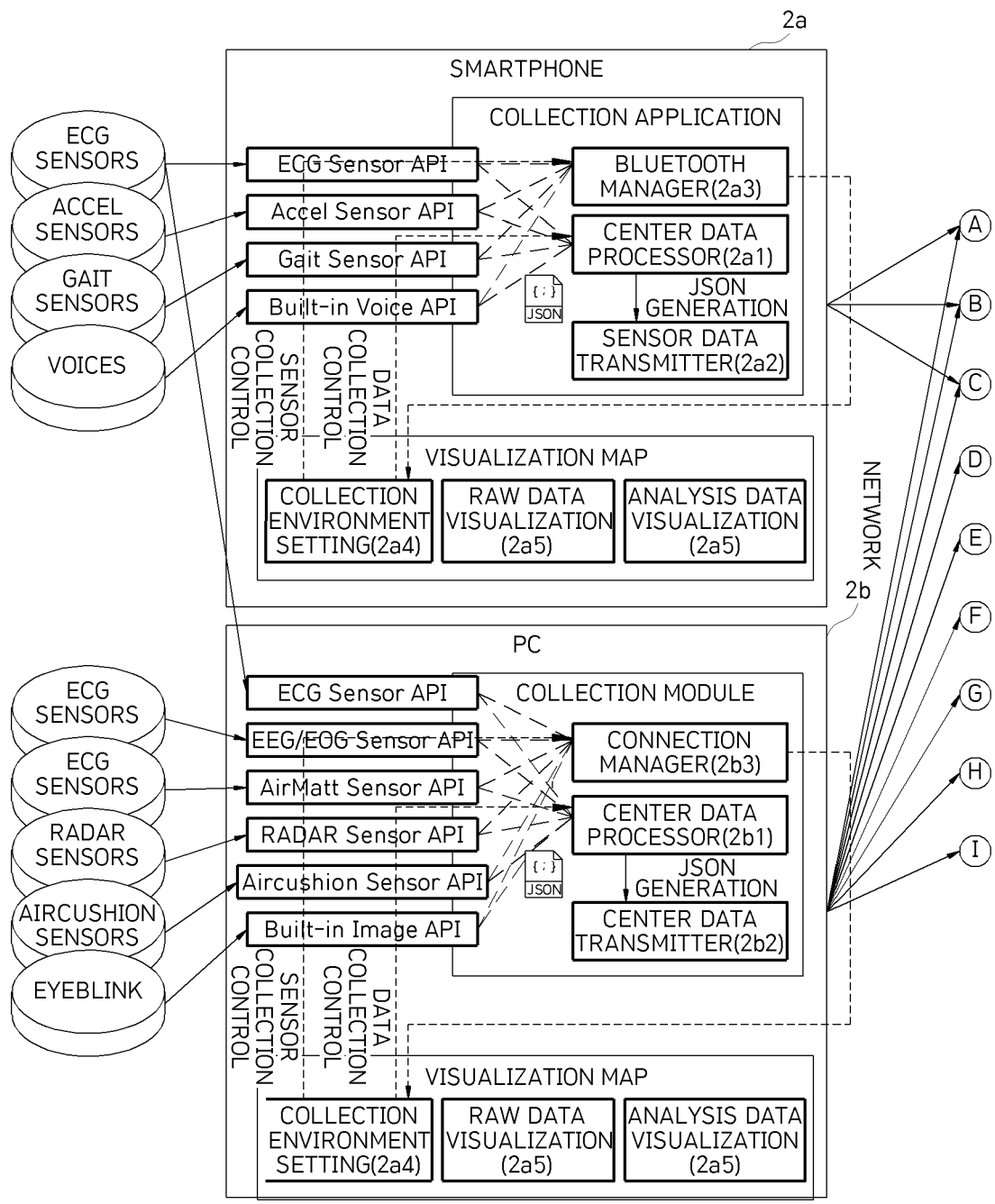
FIG. 2A and 2B are diagram for describing a biosignal data collector according to an embodiment of the present invention.
Figure 2B:
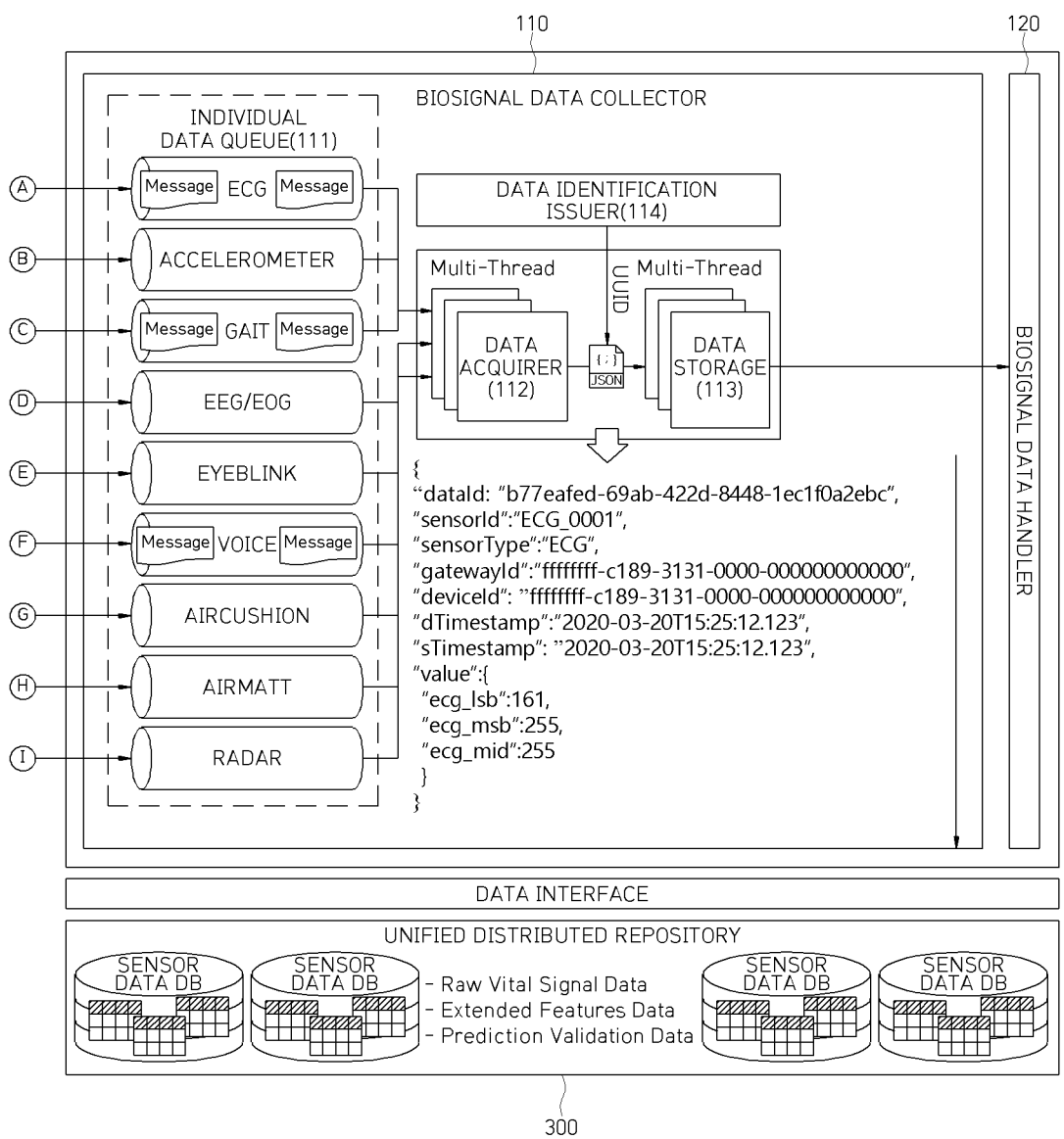

FIG. 2A and 2B are diagram for describing a biosignal data collector 110 according to an embodiment of the present invention.

The biosignal data collector 110 receives and enqueues the biosignal data collected through the user terminal 2. The biosignal data collector 110 converts biosignal data collected through the user terminal 2 into a standardized format for each sensor in the system, enqueues the biosignal data in the sensor data database of the unified distributed repository 300, and transmits the biosignal data to the biosignal data handler 120

Meanwhile, in an embodiment of the present invention, the user terminal 2 means a computer device or a telecommunication device such as a smartphone, a tablet, a personal digital assistant (PDA), a laptop, a desktop, or a server capable of collecting sensor data, and in the description of the present invention, examples of a smartphone 2a and a personal computer (PC) 2b have been described.

Referring to FIG. 2A and 2B, the smartphone 2a collects individual biosignal data from each sensor (for example, electrocardiogram (ECG), acceleration gait, voice, etc.) application programming interface (API).

The sensor data processor 2a1 of the smartphone 2a serves to receive an output of the individual sensor API to generate an integrated sensor data format. The biosignal data so generated is transmitted from a sensor data transmitter 2a2 to a server (disease prediction system) through a predetermined network (for example, 5G, Long Term Evolution (LTE), Wi-Fi, etc.).

A Bluetooth manager 2a3 performs pairing of the smartphone 2a and an individual sensor, and Bluetooth is only an example in the connection method. Therefore, it goes without saying that various pairing methods may be applied.

A visualization application of the smartphone 2a serves to visualize raw data collected from the smartphone 2a and data analyzed through the server. The visualized result may be provided through a raw data visualization module 2a5 and an analysis data visualization module 2a6.

A collection environment setting module 2a4 serves to adjust environment variables of the Bluetooth manager 2a3 and the sensor data processor 2a1 of the collection application.

Similarly, in the case of the PC 2b, individual biosignal data is collected from each sensor (for example, ECG, electroencephalogram/electrooculography (EEG/EOG), AirMatt, RADAR, Aircushion, EYEBLINK, etc.) API.

The sensor data processor 2b1 serves to receive an output of the individual sensor API to generate an integrated sensor data format. The biosignal data so generated is transmitted from a sensor data transmitter 2b2 to the server (disease prediction system) through the predetermined network (for example, 5G, LTE, Wi-Fi, etc.).

A connection manager 2b3 manages a connection between a PC and individual sensors.

A visualization module of the PC 2b serves to visualize the raw data collected from the PC 2b and the data analyzed through the server. The visualized result may be provided through a raw data visualization module 2b5 and an analysis data visualization module 2b6.

A collection environment setting module 2b4 serves to adjust environment variables of the connection manager 2b3 and the sensor data processor 2b1 of the collection module.

As such, the biosignal data collected through the user terminal 2 is transmitted to the biosignal data collector 110 of the first system unit 100.

The biosignal data collector 110 includes an individual sensor data queue 111, a data acquirer 112, and a data storage 113.

The individual sensor data queue 111 classifies the collected biosignal data for each sensor and enqueues the classified biosignal data for each sensor.

Table 1 below shows an example of the format of the ECG biosignal data enqueued in the individual sensor data queue 111.

TABLE 1

```
{
  "sensorId": "ECG_01",        //Sensor ID
  "sensorType":"ecg",          //SensorType (ECG, FOOT, EEG/EOG etc.)
  "gatewayId":" ffffffff-c189-3131-0000-000000000000",
                               //Gateway ID: Collection gateway ID
  "deviceId":" ffffffff-c189-3131-0000-000000000000",
                               //deviceId: Transmission device ID
  "dTimestamp":" 2020-03-20T15:25:12.123". //Device transmission time
  "sTimestamp": "2020-03-20T15:25:12.123", //Sensor data sensing time
  "value":{ //Data for individual sensor - JSON format
     "ecg_lsb": 161,
     "ecg_msb": 255,
     "ecg_mid": 255
  }
}
```

The data acquirer 112 driven in a multi-thread environment dequeues the biosignal data enqueued in the individual sensor data queue 111 and adds a universally unique identifier (UUID)-based unique data ID issued from a data ID issuer 114 to the biosignal data in the form of a key value. Table 2 below shows an example of the format of the ECG biosignal data for which the data ID is issued.

TABLE 2

```
{
  "dataId":"b77eafed-69ab-422d-8448-1ec1f0a2eb8c",
  "sensorId": "ECG_0001",
  "sensorType": "ECG",
  "gatewayId": "ffffffff-c189-3131-0000-000000000000",
```

TABLE 2-continued

```
      "deviceId": "ffffffff-c189-3131-0000-000000000000",
      "dTimestamp": "2020-03-20T15:25:12.123",
      "sTimestamp": "2020-03-20T15:25:12.123",
      "value": {
         "ecg_lsb": 161,
         "ecg_msb": 255,
         "ecg_mid": 255
      }
   }
```

The data storage 113 driven in the multi-thread environment enqueues the biosignal data to which the key value is added and transmits the enqueued biosignal data to the biosignal data handler 120 and the sensor data database of the unified distributed repository 300 in parallel.

Figure 3:
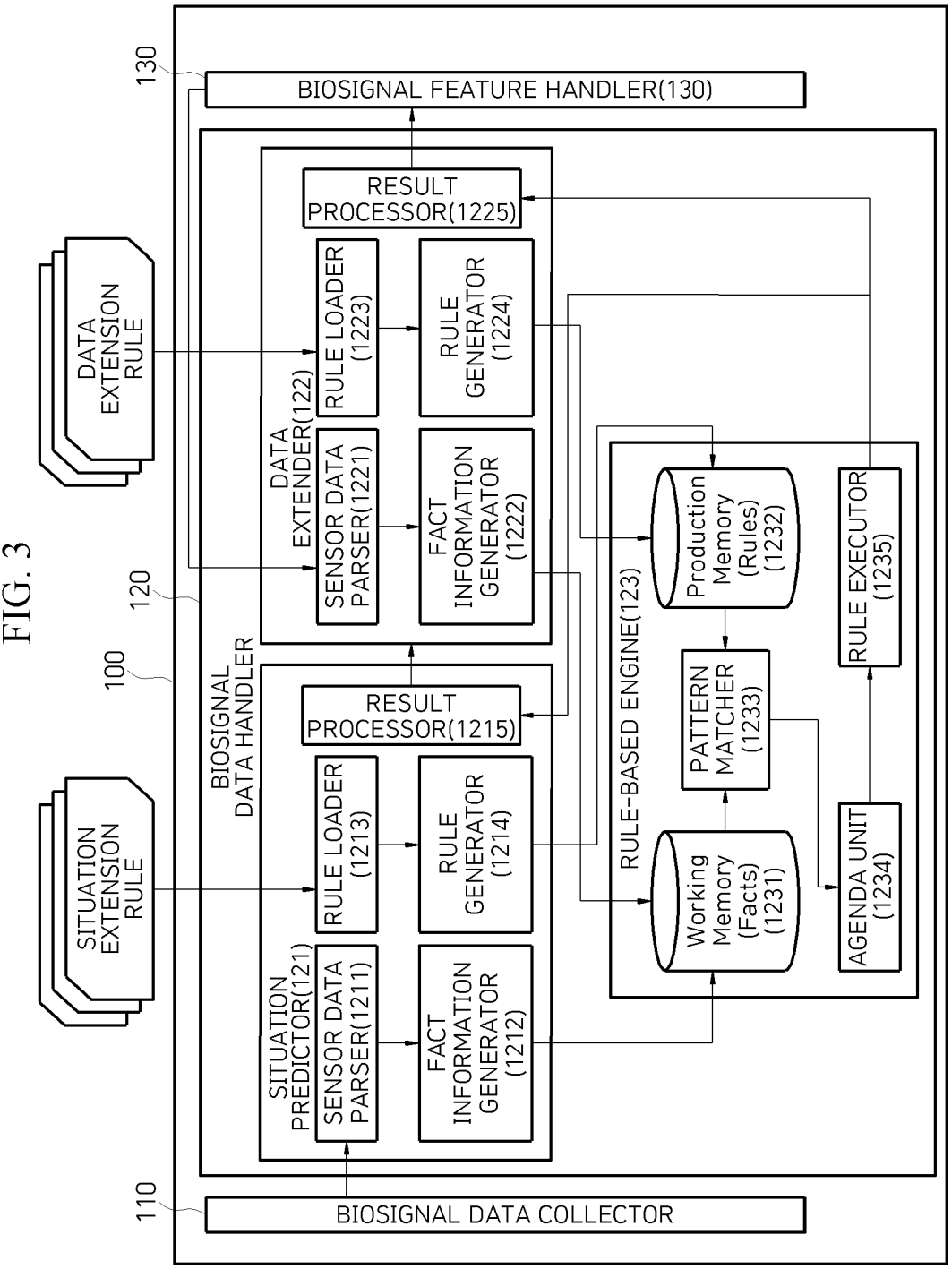
FIG. 3 is a diagram for describing a biosignal data handler according to an embodiment of the present invention.

FIG. 3 is a diagram for describing the biosignal data handler 120 according to an embodiment of the present invention.

The biosignal data handler 120 generates the corresponding service information and data extension information based on the biosignal data.

The biosignal data handler 120 includes a situation predictor 121, a data extender 122, and a rule-based engine 123.

A data parser 1211 of the situation predictor 121 parses the biosignal data collected from the biosignal data collector 110. A factual information generator 1212 generates fact information based on the parsed biosignal data and stores the generated fact information in a database 1231 (working memory) of the rule-based engine 123.

A rule loader 1213 reads predetermined situation prediction rule information from the outside. Here, the situation prediction rule information means rule information for determining a predetermined situation such as sleeping, driving, and walking. Table 3 below is a diagram illustrating an example of the situation prediction rule information.

TABLE 3

```
{
   [
      /**
      If deviceId is "ffffffff-c189-3131-0000-000000000000",
      Walking"
      */
      {
         "RuleID": "Walking_001", //Rule ID
         "Rule-Head":["deviceId".value
            == "ffffffff-c189-3131-0000-000000000000"], //Rule Condition
         "Rule-Body:"Walking" //Rule Consequence
      },
      /**
      If deviceId is "b77eafed-69ab-422d-8448-1ec1f0a2eb8c",
      Walking"
      */
      {
         "RuleID": "Walking_002",
         "Rule-Head":["deviceId".value
            == "b77eafed-69ab-422d-8448-1ec1f0a2eb8c"],
         "Rule-Body:"Walking"
      },
      /**
      If "sTimestamp".getHour is 0 to 7 o'clock, Sleeping
      */
      {
         "RuleId": "Sleep_001",
         "Rule-Head":["sTimestamp".value.getHour >= 0,
"sTimestamp".value. getHour <= 7],
         "Rule-Body:"Sleeping"
      },
      /**
      If "sensorType" is "AIRMATT", Driving
      */
```

TABLE 3-continued

```
      {
         "RuleId": "Driving_001",
         "Rule-Head":["sensorType".value == "AIRMATT"],
         "Rule-Body:"Driving"
      }
   ]
}
```

The rule generator 1214 generates compatibility rule information based on the read situation prediction rule information and stores the generated compatible rule information in a database 1232 (production memory).

The rule-based engine 123 stores the fact information and the compatible rule information in each database 1231 and 1232, performs a pattern matching process in a pattern matcher 1233 based on the fact information and the rule information, and stores the matched rule in the agenda unit 1234.

Also, a rule executor 1235 of the rule-based engine 123 executes the rule stored in the agenda unit 1234 and returns the rule execution result to the situation predictor.

Accordingly, the result processor 1215 of the situation predictor 121 generates service information corresponding to the biosignal data based on the rule execution result. The biosignal data is tagged with the service information so generated. Table 4 below shows an example of service information according to the performance result of the situation predictor 121.

TABLE 4

```
{
   "dataId:"b77eafed-69ab-422d-8448-1ec1f0a2eb8c",
   "sensorId": "ECG_0001",
   "sensorType": "ECG",
   "gatewayId": "ffffffff-c89-3131-0000-000000000000",
   "deviceId": "ffffffff-c189-3131-0000-000000000000",
   "dTimestamp": "2020-03-20T15:25:12.123",
   "sTimestamp": "2020-03-20T15:25:12.123",
   "service":"walking", //Added service information
   "value": {
      "ecg_lsb": 161,
      "ecg_msb": 255,
      "ecg_mid": 255
   }
}
```

In addition, the data extender 122 of the biosignal data handler 120 parses the service information that is the output result of the situation predictor 121 through the data parser 1221, and the fact information generator 1222 generates the fact information based on the parsed service information and stores the generated fact information in the database 1231 of the rule-based engine 123.

The rule loader 1223 reads predetermined situation prediction rule information from the outside. Here, the data extension rule information refers to information, such as driving posture, gait balance, and drowsiness, which is abstracted one step more, from quantified biosignal data through the rule. Table 5 below shows an example of the data extension rule information.

TABLE 5

```
{
   [
      /**
      If "sensorType" is EYEBLINK, and blink "count" is less than 15,
      driving_drowsy
```

TABLE 5-continued

```
*/
{
  "RuleId": "Driving_Data_Extended_001",
  "Rule-Head":[ "sensorType".value == "EYEBLINK",
     "count".value < 15],
  "Rule-Body:" "driving_drowsy"
},
/**
  If "sensorType" is Foot, and "walking speed" is 0.1 to 0.76,
  walking_abnormal
*/
{
  "RuleId": "Foot_Data_Extended_001",
  "Rule-Head":[ "sensorType".value == "Foot",
  "walkingspeed".value > 0.1, "walkingspeed".value < 0.76],
  "Rule-Body:" "walking_abnormal"
},
]
}
```

The rule generator 1224 generates the compatible rule information based on the read data extension rule information and stores the generated compatible rule information in the database 1232 (production memory) of the rule-based engine 123.

The rule-based engine 123 stores the fact information and the compatible rule information in each database 1231 and 1232, performs the pattern matching process in the pattern matcher 1233 based on the fact information and the compatible rule information, and stores the matched rule in the agenda unit 1234.

Also, the rule executor 1235 of the rule-based engine 123 executes the rule stored in the agenda unit 1234 and returns the rule execution result to the data extender 122.

Accordingly, the result processor 1225 of the data extender 122 generates the data extension information corresponding to the biosignal data based on the rule execution result. The biosignal data is tagged with the data extension information so generated. Table 6 below shows an example of the data extension information according to the execution result of the data extender 122.

TABLE 6

```
{
  "dataId":"b77eafed-69ab-422d-8448-1ec1f0a2eb8c",
  "sensorId": "ECG_0001",
  "sensorType": "ECG",
  "gatewayId": "ffffff-c189-3131-0000-000000000000",
  "deviceId": "ffffff-c189-3131-0000-000000000000",
  "dTimestamp": "2020-03-20T15:25:12.123",
  "sTimestamp": "2020-03-20T15:25:12.123",
  "service":"walking",
  "value": {
  "ecg_lsb": 161,
  "ecg_msb": 255,
  "ecg_mid": 255
  }
  "features:{       //Added data extension information
     "extended":["walking_abnormal", "driving_drowsy"]
  },
}
```

The biosignal data handler 120 according to the embodiment of the present invention is provided in a structure in which a user can add, modify, and delete the situation prediction rule information and the data extension rule information based on a traditional rule-based engine.

Figure 4:
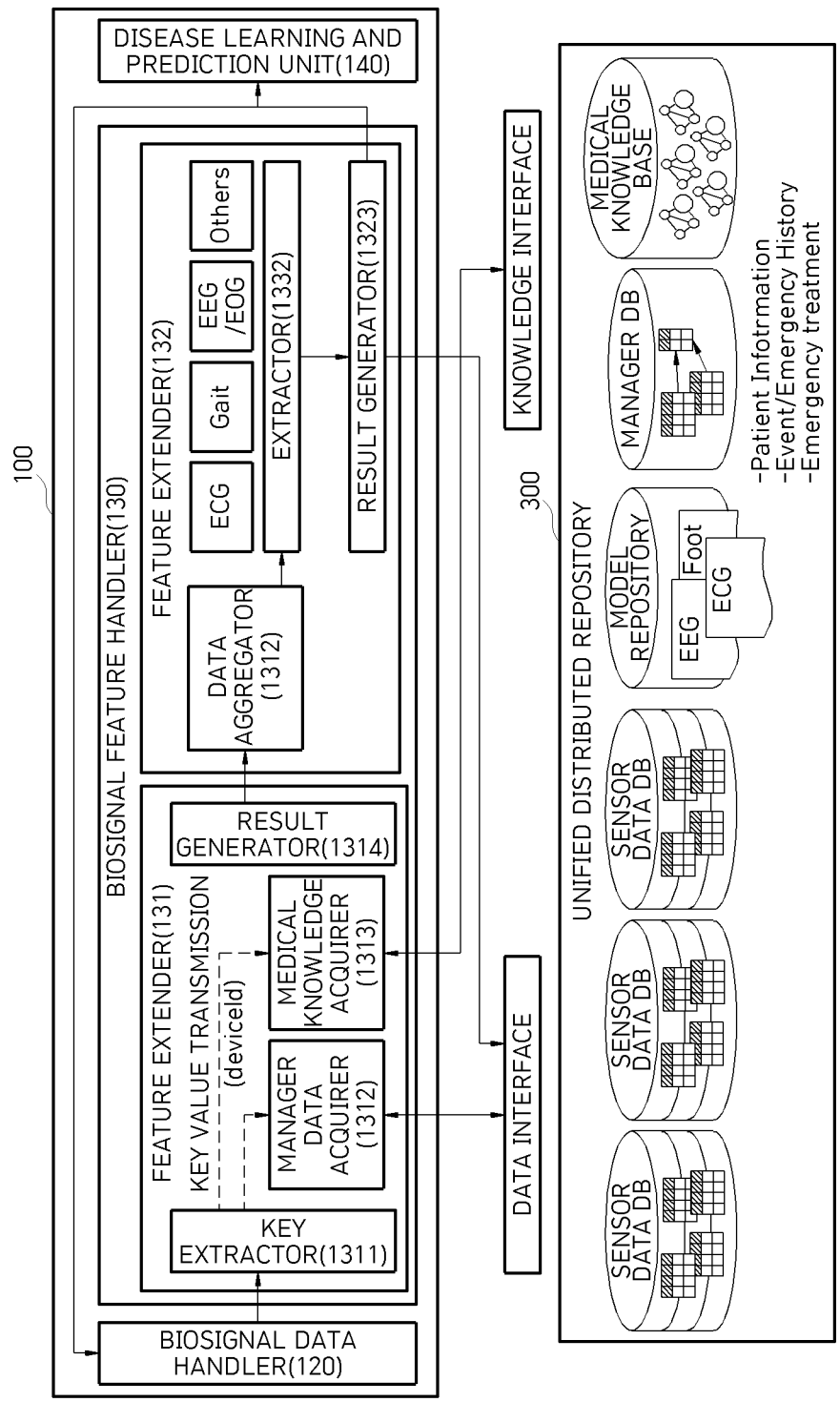
FIG. 4 is a diagram for describing a biosignal feature handler according to an embodiment of the present invention.

FIG. 4 is a diagram for describing the biosignal feature handler 130 according to an embodiment of the present invention.

The biosignal feature handler 130 extends medically meaningful feature information (hereinafter, referred to as medical feature information) from a series of collected pieces of biosignal data, and extracts the medical feature information corresponding to the biosignal data collected for a predetermined period among the extended medical feature information. The biosignal feature handler 130 extends the medical feature information by being linked with the medical knowledge base and the manager database of the unified distributed repository 300 and extracts the medical feature information based on the extended medical feature information.

The biosignal feature handler 130 includes a feature extender 131 and a feature extractor 132.

The feature extender 131 extracts a key value corresponding to data ID assigned to the biosignal data to obtain additional information (for example, patient ID, gender, age, etc.) of a user corresponding to the key value from the manager database of the unified distributed repository 300. In addition, the feature extender 131 acquires disease information (for example, possessed disease, current symptom, suspected part, etc.) of a user corresponding to the key value from the medical knowledge base of the unified distributed repository 300.

The feature extender 131 extends the medical feature information based on each piece of additional information and disease information acquired in this way. Table 7 below shows an example of the medical feature information extension result performed by the feature extender 131.

TABLE 7

```
{
  "dataId":"b77eafed-69ab-422d-8448-1ec1f0a2eb8c",
  "sensorId": "ECG_0001",
  "sensorType": "ECG",
  "gatewayId": "ffffff-c189-3131-0000-000000000000",
  "deviceId": "ffffff-c189-3131-0000-000000000000",
  "dTimestamp": "2020-03-20T15:25:12.123",
  "sTimestamp": "2020-03-20T15:25:12.123",
  "service":"walking",
  "value": {
  "ecg_lsb": 161,
  "ecg_msb": 255,
  "ecg_mid": 255
  }
  "features:{
     "extended":["walking_abnormal", "driving_drowsy"],
     "userId":"xxxxxxx",              //Patient ID
     "gender":"male",                  //Patient gender
     "age":67,                         //Patient age
     "diseases":["xxxx, xxxx, xxxx] ", //Possessed diseased of
                                       patient
     "symptom":"[xxxx, xxxx, xxxx] ",  //Current symptom of patient
     "portion":"[xxxx, xxxx, xxxx] ",  //Suspect part of patient
  },
}
```

The feature extractor 132 clusters the biosignal data for a predetermined period and extracts the medical feature information corresponding to the biosignal data based on the extended medical feature information. Table 7 below shows an example of the medical feature information extracted by the feature extractor 132.

TABLE 8

```
{
  "featureId": "b77eafed-69ab-422d-8448-1ec1f0a2eb8c",
  "relatedDataId": ["xxxxxx", "xxxxxx","xxxxxx"],
  "sTimestamp": "2020-03-20T15:25:12.123",
  "sensorType": "Foot",
```

TABLE 8-continued

```
    "service": "walking",
    "features": {
      "extended": [" driving_drowsy ","walking_abnormal"],
      "userId": "xxxxxx",
      "gender": "male",
      "age": 67,
      "diseases": ["xxxxxx", "xxxxxx","xxxxxx"],
      "symptoms": ["xxxxxx", "xxxxxx","xxxxxx"],
      "portion": ["xxxxxx", "xxxxxx","xxxxxx"],
      "singlesupport": 0,
      "doublesupport": 0.01,
      "steplength": 0.01,
      "steptime": 0.01,
      "stridelength": 0.01,
      "stridetime": 0.01,
      "cadence": 0.01,
      "walkingspeed": 0.01,
      "stepcount": 0.01,
      "footoff": 0.01,
      "oppositefootcontact": 0.01,
      "oppositefootoff": 0.01,
      "caloricconsumption": 0.01
    }
  }
```

The biosignal data handler 120 may execute the situation predictor 121 and the data extender 122 using only the biosignal data to generate the service information and the data extension rule and may further use the extracted medical feature information to generate the service information and the data extension information.

Figure 5:
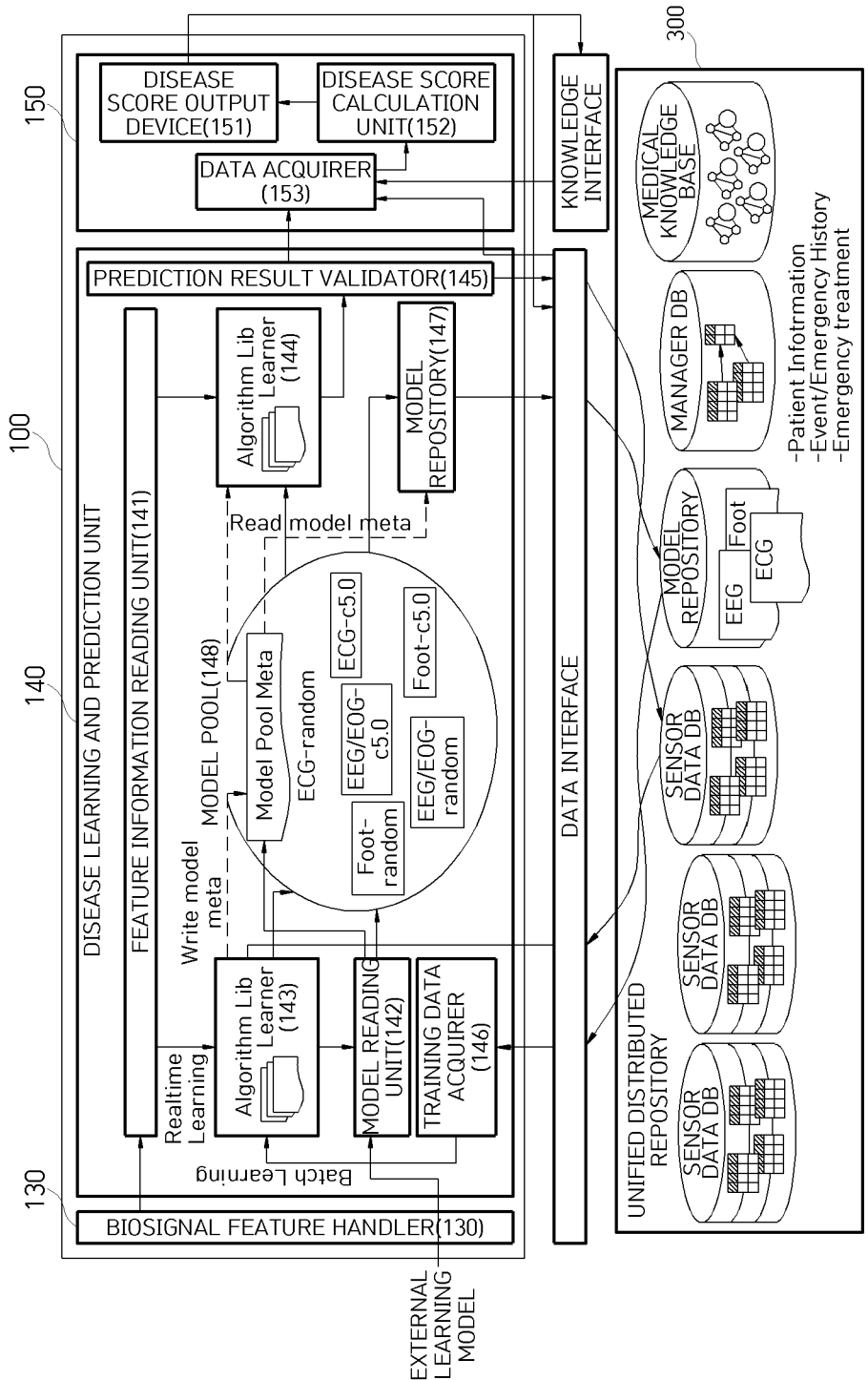
FIG. 5 is a diagram for describing a disease learning and prediction unit and a disease score calculation unit according to an embodiment of the present invention.

FIG. 5 is a diagram for describing the disease learning and prediction unit 140 and the disease score calculation unit 150 in an embodiment of the present invention.

The disease learning and prediction unit 140 trains the prediction model based on the extracted medical feature information and generates the disease prediction result based on the prediction model. The disease score calculation unit 150 calculates a disease score based on the disease prediction result, the medical feature information, and the medical findings (personal health checkup information, disease, symptoms, body parts, etc.) stored in the medical knowledge base.

Specifically, the disease learning and prediction unit 140 includes a feature information reading unit 141, a model reading unit 142, a learner 143, a predictor 144, and a prediction result validator 145.

The feature information reading unit 141 collects the medical feature information extracted by the biosignal feature handler 130 and determines the learner 143 and the predictor 144 corresponding to the key value (for example, sensor type, service information, etc.) corresponding to the data ID of the biosignal data. Then, the biosignal data and the medical feature information are transmitted to the determined learner 143 and predictor 144.

The model reading unit 142 reads the prediction model trained from the outside and the prediction model stored in the model repository of the unified distributed repository 300. The model reading unit 142 adds model information of the read prediction model to model metadata and stores the model information in a model pool 148.

The learner 143 includes the prediction model stored in the model pool 148 using the model metadata and performs the training of the prediction model based on each piece of information provided from the feature information reading unit 141 or the learning data acquirer 146. The prediction model trained by the learner 143 is stored in the model pool 148.

The predictor 144 includes the prediction model stored in the model pool 148 using the model metadata and generates a disease prediction result through the trained prediction model based on each piece of information provided from the feature information reading unit 141.

The prediction result validator 145 tags a "validation" item of the disease prediction result with expert's validation result information on the disease prediction result generated by the predictor 144.

The model storage 147 serves to store the models existing in the model pool 148 in the model repository of the unified distributed repository 300.

The disease score calculation unit 150 calculates the disease score based on the disease (stroke) prediction result, the medical feature information, and the medical findings (personal health checkup information, disease, symptoms, body parts, etc.) stored in the medical knowledge base. The calculated disease score is stored in the unified distributed repository 300 and transmitted to a medical knowledge annotator 210 to be described below.

Referring back to FIG. 1, the second system unit 200 of the disease prediction system 1 according to the embodiment of the present invention includes a medical knowledge annotator 210, a medical knowledge Q&A processor 220, a knowledge processing engine 230, and a medical knowledge augmenter 240.

Figure 6:
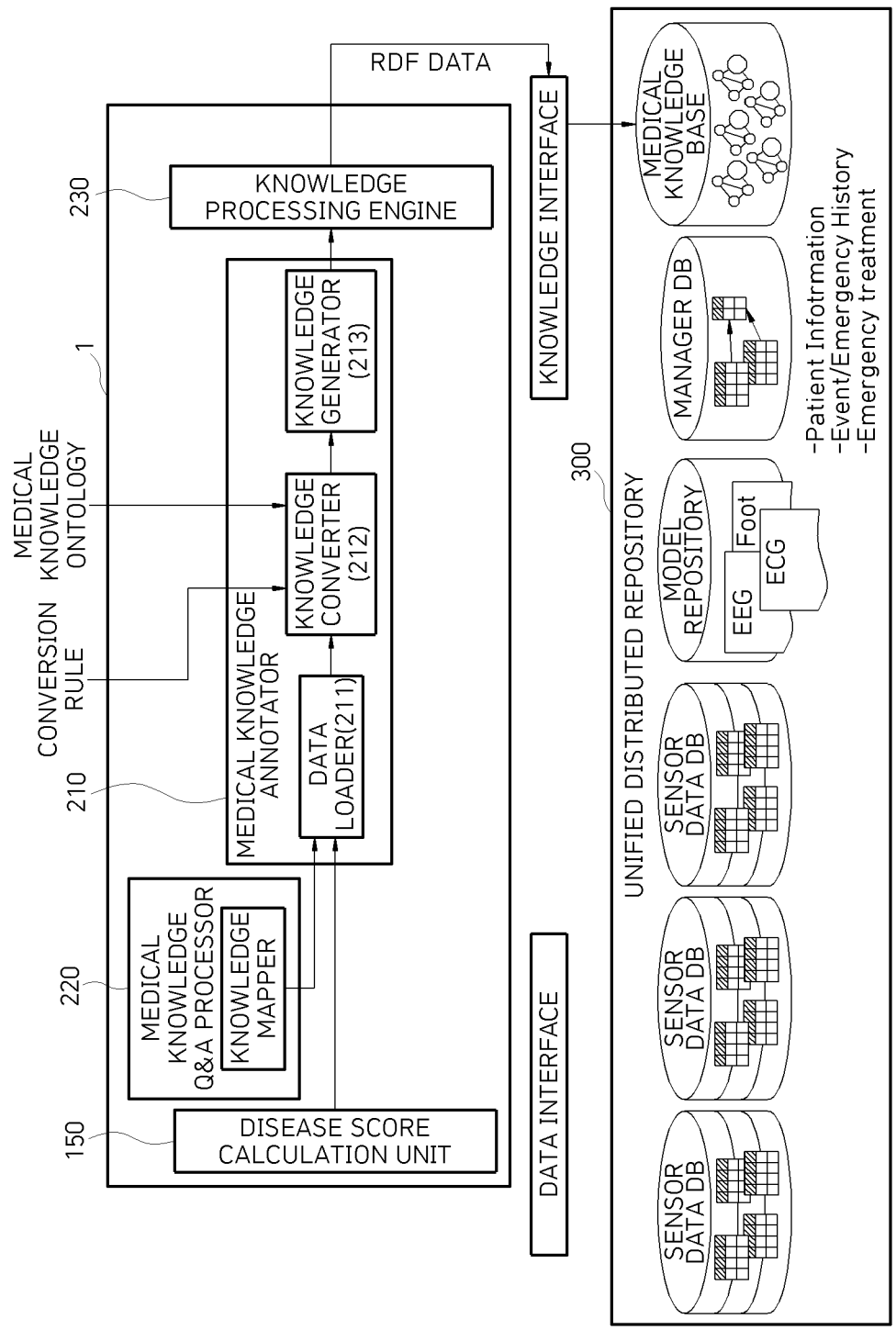
FIG. 6 is a diagram for describing a medical knowledge annotator according to an embodiment of the present invention.

FIG. 6 is a diagram for describing the medical knowledge annotator 210 according to an embodiment of the present invention.

The medical knowledge annotator 210 generates medical knowledge data having a predetermined type based on the calculated disease score and the user query.

The medical knowledge annotator 210 performs semantic annotation. In this case, the semantic annotation means generating new semantic metamodels (resource description framework (RDF), RDF schema (RDFS_, and web ontology language (OWL)) using ontology-based schema information for the purpose of deriving and extending new knowledge from existing legacy data.

The medical knowledge annotator 210 performs a semantic annotation function on a query morpheme that is an analysis result of a user query in a natural language form. In addition, in order to link the calculated disease score with the medical knowledge base, the medical knowledge annotator 210 serves to generate the medical knowledge data (RDF, etc.) using the medical knowledge ontology and add the generated medical knowledge data to the medical knowledge base.

To this end, the medical knowledge annotator 210 includes a data loader 211, a medical knowledge data converter 212, and a medical knowledge data generator 213.

The data loader 211 reads the disease score calculated by the disease score calculation unit 150 and the query morpheme analyzing the user query. In this case, the query morpheme is provided from the medical knowledge Q&A processor 220 to be described below.

The medical knowledge data converter 212 converts the disease score and the query morpheme into the medical knowledge data based on a predetermined conversion rule and a medical knowledge ontology.

The medical knowledge data generator 213 generates the converted medical knowledge data as the medical knowledge data (RDF, etc.) having a predetermined type and transmits the medical knowledge data to the knowledge processing engine 230. The medical knowledge data finally generated by the medical knowledge data generator 213 is added to the medical knowledge base through the knowledge processing engine 230.

Figure 7:
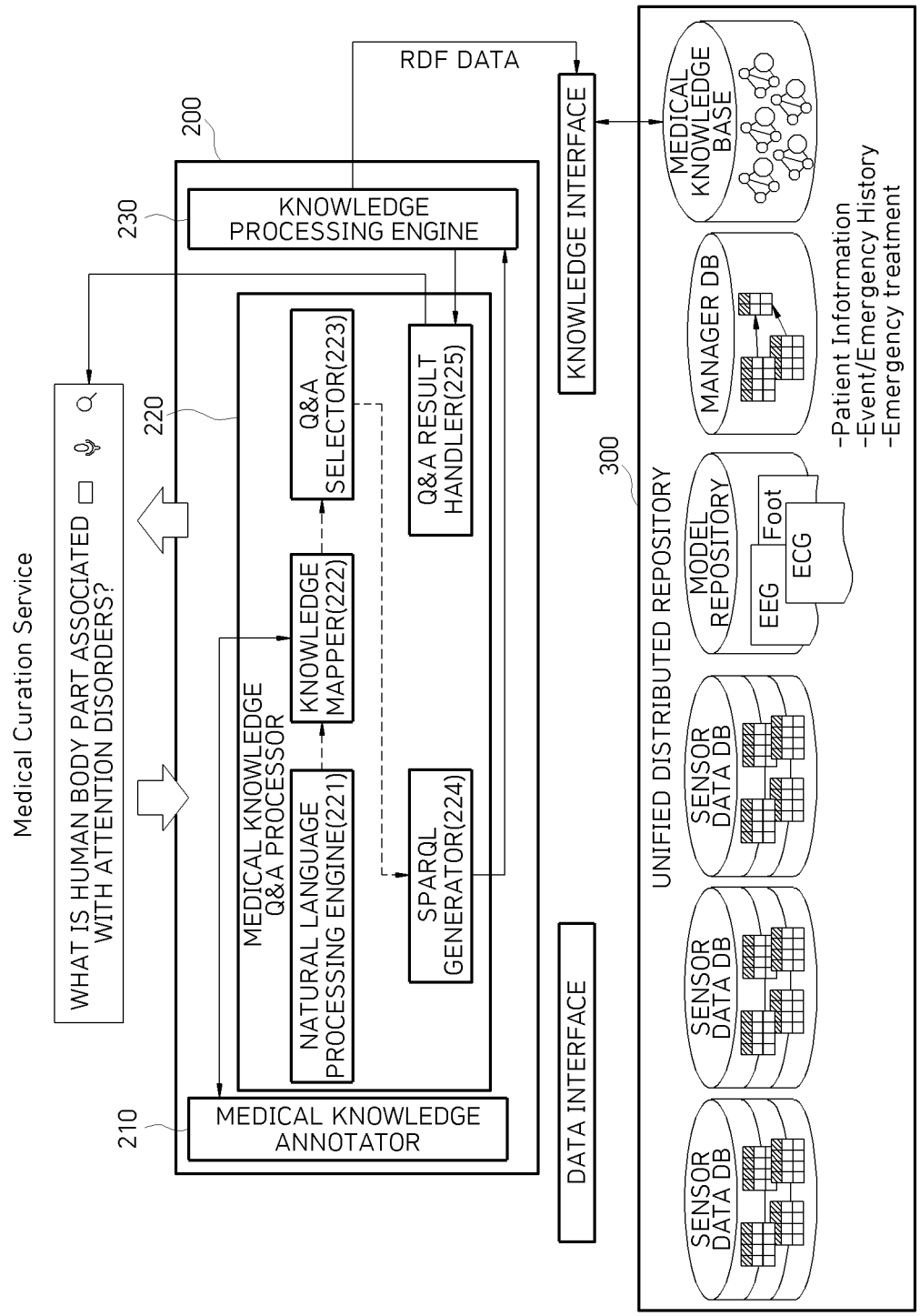
FIG. 7 is a diagram for describing a medical knowledge Q&A processor according to an embodiment of the present invention.

FIG. 7 is a diagram for describing the medical knowledge Q&A processor 220 according to an embodiment of the present invention.

The medical knowledge Q&A processor 220 includes a natural language processing engine 221, a knowledge mapper 222, a Q&A selector 223, a SPARQL protocol and RDF query language (SPARQL) generator 224, and a Q&A result handler 225.

The natural language processing engine 221 extracts the query morpheme by analyzing the user query in the natural language form.

The knowledge mapper 222 serves to map the extracted morpheme to be linked to the medical knowledge base.

The Q&A selector 223 selects the user query and a response corresponding to the user query, and the SPARQL generator 224 derives an ontology rule-based SPARQL pattern using the medical knowledge base extended through the selected user query and response. The Q&A result handler 225 provides the SPARQL execution result.

Figure 8:
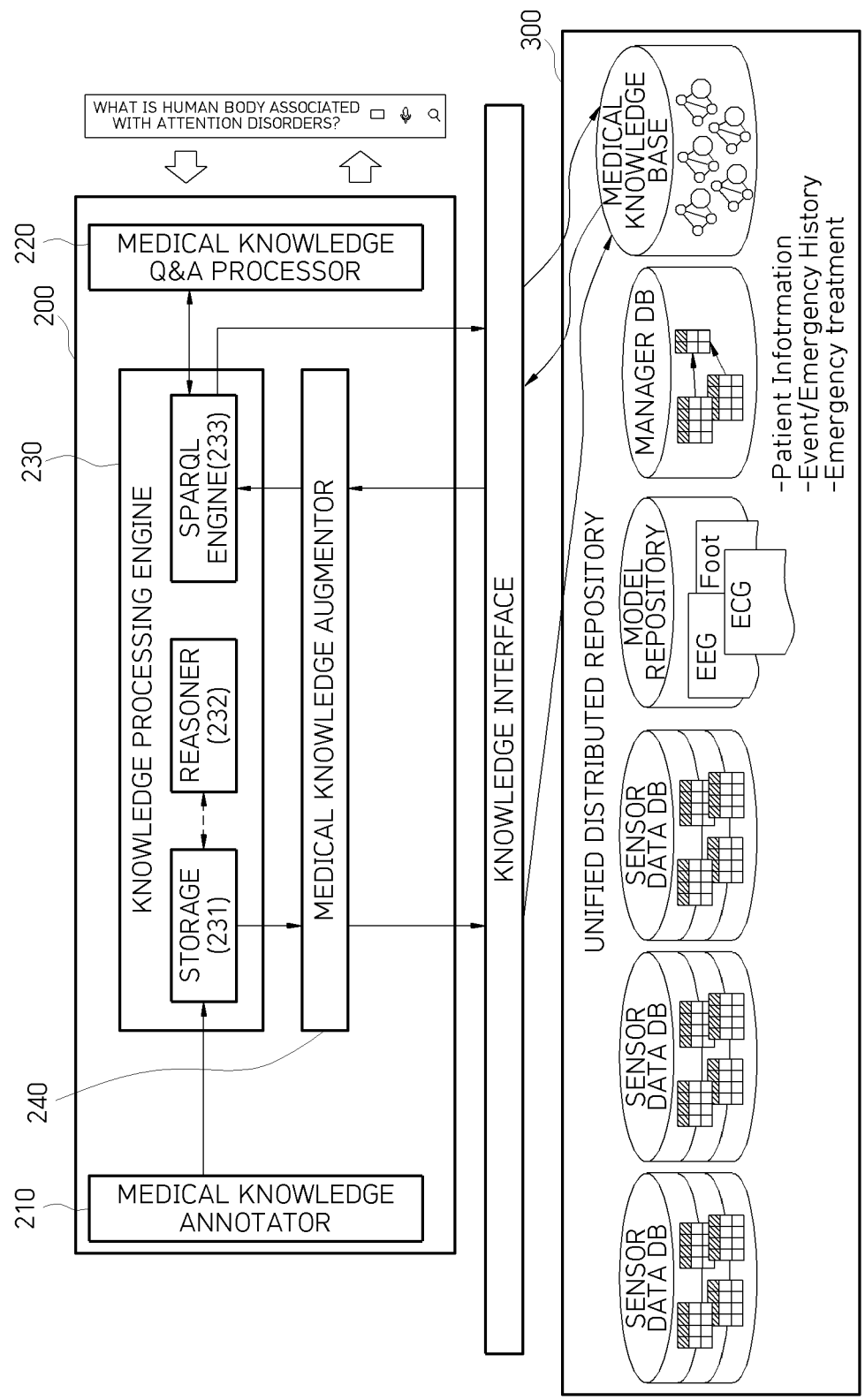
FIG. 8 is a diagram for describing a knowledge processing engine according to an embodiment of the present invention.

FIG. 8 is a diagram for describing the knowledge processing engine 230 according to an embodiment of the present invention.

The knowledge processing engine 230 serves to input, delete, inquire, and reason the medical knowledge data and generates the SPARQL execution result and provides the generated execution result to the medical knowledge Q&A processor 220.

For this, the knowledge processing engine 230 includes a storage 231, a reasoner 232, and a SPARQL engine 233.

The storage 231 serves to input the medical knowledge data generated from the medical knowledge annotator 210 to the medical knowledge base and read the medical knowledge data. In addition, the storage 231 includes an ontology schema of an externally modeled medical knowledge base and serves to configure medical knowledge data of the medical knowledge base through linkage with the medical knowledge base.

The reasoner 232 defines a predetermined ontology rule (in the form of RDF, RDFS, OWL, etc.) and serves to extend the medical knowledge data by performing reasoning through the medical knowledge data based on the ontology rule. That is, the reasoner 232 loads and installs the ontology rule therein, and then, when new medical knowledge data is input, performs reasoning along with the existing medical knowledge data to extend knowledge.

The SPARQL engine 233 executes SPARQL, which is a knowledge standard query language for medical knowledge data generated by the SPARQL generator 234 of the medical knowledge Q&A processor 220, and transmits the SPARQL execution result to the Q&A result handler 235.

Referring to FIGS. 1 and 8, the medical knowledge augmenter 240 serves to perform machine learning based on the medical knowledge data stored in the medical knowledge base to generate the learning model and automatically augments knowledge when new medical knowledge data is added based on the generated learning model.

The processing result of the knowledge processing engine 230 for storing, reasoning, and querying the medical knowledge base is transmitted to and processed by the medical knowledge augmenter 240 that performs knowledge embedding and knowledge completion functions in a background and bootstrap manner. In addition, the processing result is stored in the unified distributed repository 300.

The medical knowledge augmenter 240 performs the training and reasoning process of knowledge embedding based on the data processed by the traditional knowledge processing engine (knowledge changer, knowledge reasoner, and knowledge query engine), triggers the newly derived medical knowledge based on the training of knowledge embedding and the reasoning process again in the traditional knowledge processing manner, and operates in the bootstrap manner that triggers the knowledge embedding process again.

Figure 9:
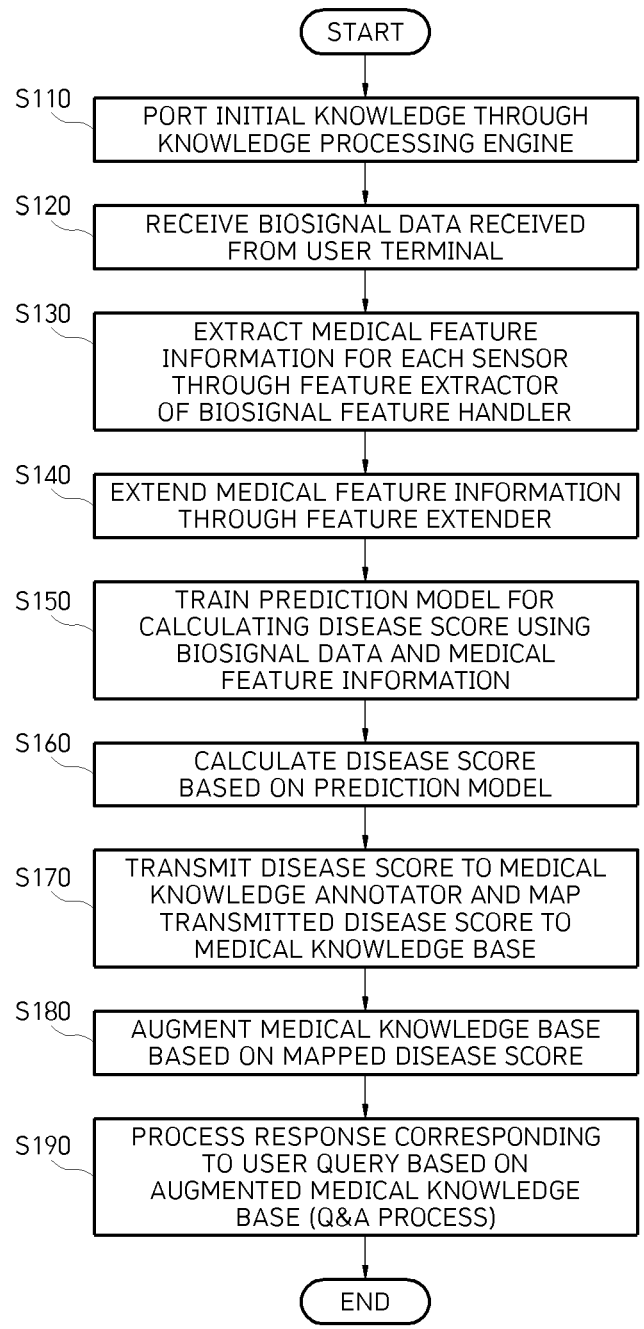
FIG. 9 is a flowchart of a method of predicting disease based on biosignal data and medical knowledge base convergence according to an embodiment of the present invention.

FIG. 9 is a flowchart of a method of predicting disease based on biosignal data and medical knowledge base convergence according to an embodiment of the present invention.

Meanwhile, each operation illustrated in FIG. 9 may be understood to be performed by the disease prediction system 1 in FIGS. 1 to 8 but is not necessarily limited thereto.

In the disease prediction method according to the embodiment of the present invention, first, initial knowledge (a medical knowledge base ontology, a reasoning rule, and a conversion rule) are ported through a knowledge processing engine (S110).

Next, the biosignal data received from the user terminal is received through the biosignal data collector (S120).

Next, the medical feature information is extracted for each sensor through the feature extractor of the biosignal feature handler (S130), and the medical feature information is extended through the feature extender (S140).

Next, the prediction model for calculating the disease score is trained using the biosignal data and the medical feature information (S150), and the disease score is calculated based on the trained prediction model (S160).

Next, the calculated disease score is transmitted to the medical knowledge annotator and mapped to be linked to the medical knowledge base (S170), and the medical knowledge base is augmented through the medical knowledge augmenter and the knowledge processing engine based on the mapped disease score and medical knowledge base (S180).

The Q&A process for processing the response corresponding to an input user query is performed based on the augmented medical knowledge base (S190).

In this case, the operations S140 to S180 are circulated in the bootstrap manner.

Meanwhile, in the above description, operations S110 to S190 may be further divided into additional operations or combined into fewer operations according to an implementation example of the present invention. Also, some operations may be omitted if necessary, and an order between the operations may be changed. Meanwhile, the contents of the disease prediction system 1 of FIGS. 1 to 8 may be applied to the contents of FIG. 9 as well.

The method of predicting disease based on biosignal data and medical knowledge base convergence according to the embodiment of the present invention described above may be implemented as a program (or application) and stored in a medium to be executed in combination with a computer that is hardware.

In order for the computer to read the program and execute the methods implemented as the program, the program may include a code coded in a computer language such as C, C++, JAVA, Ruby, or machine language that the processor (central processing unit (CPU)) of the computer may read through a device interface of the computer. Such code may include functional code related to a function or such defining functions necessary for executing the methods and include an execution procedure related control code necessary for the processor of the computer to execute the functions according to a predetermined procedure. In addition, the code may further include a memory reference related code for which location (address street number) in an internal or external memory of the computer the additional information or media necessary for the processor of the computer to execute the functions is to be referenced at. In addition, when the processor of the computer needs to communicate with any other computers, servers, or the like located remotely in order to execute the above functions, the code may further include a communication-related code for how to communicate with any other computers, servers, or the like using the communication module of the computer, what information or media to transmit/receive during communication, and the like.

The storage medium is not a medium that stores images therein for a while, such as a register, a cache, a memory, or the like but means a medium that semi-permanently stores the images therein and is readable by an apparatus. Specifically, examples of the storage medium include, but are not limited to, read-only memory (ROM), random-access memory (RAM), compact disc read-only memory (CD-ROM), a magnetic tape, a floppy disk, an optical image storage, and the like. That is, the program may be stored in various recording media on various servers accessible by the computer or in various recording media on the computer of the user. In addition, media may be distributed in a computer system connected by a network, and a computer-readable code may be stored in a distributed manner.

The above description of the present invention is for illustrative purposes, and those skilled in the art to which the present invention pertains will understand that it may be easily modified to other specific forms without changing the technical spirit or essential features of the present invention. Therefore, it is to be understood that the exemplary embodiments described hereinabove are illustrative rather than being restrictive in all aspects. For example, each component described as a single type may be implemented in a distributed manner, and similarly, components described as distributed may be implemented in a combined form.

It is to be understood that the scope of the present invention will be defined by the claims rather than the above-described description, and all modifications and alternations derived from the claims and their equivalents are included in the scope of the present invention.

What is claimed is:

1. A disease prediction system, the system comprising:
   a first system unit configured to receive, from a user terminal, biosignal data collected from at least one sensor configured to sense a biosignal and calculate a disease score from the biosignal data based on a pre-trained prediction model;
   a second system unit configured to provide medical knowledge data for the first system unit, analyze a query input from the user terminal to provide a corresponding response, and augment the medical knowledge data based on the query and response;
   a unified distributed repository that includes a database configured to enqueue the biosignal data, a manager database configured to store additional information of a user, and a medical knowledge base configured to store predetermined medical knowledge data, and
   a biosignal feature handler configured to extend medical feature information from the collected biosignal data and extract medical feature information corresponding to biosignal data collected for a predetermined period from among the extended medical feature information.

2. The system of claim 1, wherein the first system unit includes:
   a biosignal data collector configured to enqueue the collected biosignal data;
   a biosignal data handler configured to generate corresponding service information and data extension information based on the biosignal data;
   a disease learning and prediction unit configured to train a prediction model based on the extracted medical feature information and generate a disease prediction result based on the prediction model; and
   a disease score calculation unit configured to calculate a disease score based on the disease prediction result, the medical feature information, and the medical knowledge base.

3. The system of claim 2, wherein the biosignal data collector includes:
   an individual sensor data queue configured to classify the collected biosignal data for each sensor and enqueue the classified biosignal data for each sensor;
   a data acquirer configured to dequeue the biosignal data enqueued in the individual sensor data queue to add a data ID issued from a data ID issuer to the biosignal data in a form of a key value; and
   a data storage configured to enqueue the biosignal data to which the key value is added and transmit the enqueued biosignal data to the biosignal data handler and the unified distributed repository.

4. The system of claim 2, wherein the biosignal data handler includes:
   a situation predictor configured to parse the biosignal data to generate and store fact information, generate and store compatible rule information based on predetermined situation prediction rule information read from an outside, and generate service information corresponding to the biosignal data based on a rule execution result; and
   a rule-based engine configured to store the fact information and the compatible rule information in the database, perform a pattern matching process based on the fact information and the compatible rule information, and store and execute the matched rule and return a matched rule execution result to the situation predictor.

5. The system of claim 4, wherein the biosignal data handler further includes:
   a data extender configured to parse the service information to generate and store the fact information, generate and store the compatible rule information based on predetermined data extension rule information read from the outside, and generate data extension information corresponding to the biosignal data based on rule execution information, and
   the rule-based engine stores the fact information and the compatible rule information of the data expander in the database, performs the pattern matching process based on the fact information and the compatible rule information, and stores and executes the matched rule to return the matched rule execution result to the data extender.

6. The system of claim 2, wherein the biosignal feature handler includes:
   a feature extender configured to extract a key value corresponding to a data ID from the biosignal data and acquire additional information and disease information of a user corresponding to the key value from the unified distributed repository to extend the medical feature information; and a feature extractor configured to cluster the biosignal data for the predetermined period and extract the medical feature information corresponding to the biosignal data based on the extended medical feature information.

7. The system of claim 6, wherein the biosignal data handler generates the corresponding service information and the data extension information based on the biosignal data and the extracted medical feature information.

8. The system of claim 2, wherein the disease learning and prediction unit includes:
a feature information reading unit configured to collect the extracted medical feature information and determine a corresponding learner and predictor through a key value corresponding to the data ID of the biosignal data;
a model reading unit configured to read a prediction model trained from the outside and a prediction model stored in the unified distributed repository and store the read prediction models in a model pool;
a learner that includes the prediction models stored in the model pool and trains the prediction models based on each piece of information provided from the feature information reading unit; and
a predictor that includes the prediction models stored in the model pool and generates a disease prediction result based on each piece of information provided from the feature information reading unit.

9. The system of claim 8, wherein the disease learning and prediction unit further includes a prediction result validator configured to tag the generated disease prediction result with expert's validation result information.

10. The system of claim 2, wherein the second system unit includes:
a medical knowledge annotator configured to generate medical knowledge data having a predetermined type based on the calculated disease score and a user query;
a medical knowledge Q&A processor configured to analyze the user query, map the analyzed user query to be linked to the medical knowledge base, and provide a result of executing SPARQL protocol and RDF query language (SPARQL) using the selected user query and response and the medical knowledge base;
a knowledge processing engine configured to input and dequeue the medical knowledge data and generate an execution result of the SPARQL; and
a medical knowledge augmenter configured to perform machine learning based on the medical knowledge data stored in the medical knowledge base to generate a learning model and augment the medical knowledge data based on the learning model when new medical knowledge data is added.

11. The system of claim 10, wherein the medical knowledge annotator includes:
a data loader configured to read the calculated disease score and a query morpheme analyzing the user query;
a medical knowledge data converter configured to convert the disease score and the query morpheme into the medical knowledge data based on a predetermined conversion rule and medical knowledge ontology; and
a medical knowledge data generator configured to generate the converted medical knowledge data as the medical knowledge data having the predetermined type and transmit the generated medical knowledge data to the knowledge processing engine.

12. The system of claim 11, wherein the medical knowledge Q&A processor includes:
a natural language processing engine configured to analyze the user query and extract the query morpheme;
a knowledge mapper configured to map the query morpheme to be linked to the medical knowledge base;
a Q&A selector configured to select the user inquiry and a response corresponding to the user inquiry;
a SPARQL generator configured to derive a pattern of ontology rule-based SPARQL using the medical knowledge base extended through the selected user query and response; and
a Q&A result handler configured to provide a result of the SPARQL execution.

13. The system of claim 12, wherein the knowledge processing engine includes:
a storage configured to input the medical knowledge data generated from the medical knowledge annotator to the medical knowledge base and read the input medical knowledge data;
a reasoner configured to define the ontology rule and perform reasoning based on the stored medical knowledge data based on the ontology rule to extend the medical knowledge data; and
a SPARQL engine configured to execute the SPARQL.

14. A disease prediction method, the method comprising:
receiving biosignal data collected from at least one sensor configured to sense biosignals through a user terminal;
obtaining extended medical feature information based on the received biosignal data;
extracting current medical feature information based on multiple biosignal data, collected over a predetermined period, and the obtained extended medical feature information;
calculating a disease score dependent on a pre-trained disease score prediction model, the received biosignal data, and the extracted current medical feature information;
generating medical knowledge data having a predetermined type based on the calculated disease score and a user query;
augmenting user medical knowledge data, pre-stored in a medical knowledge database, using the generated medical knowledge data; and
providing a response corresponding to the user query based on the augmented user medical knowledge data.

* * * * *